(12) United States Patent
Reid (10) Patent No.: US 7,497,845 B2
(45) Date of Patent: Mar. 3, 2009

(54) NEEDLE DEVICE HAVING SLIDEABLE MEMBER PROVIDING ENHANCED SAFETY

(76) Inventor: Alan Reid, 137 Armory St., Keene, NH (US) 03431

( * ) Notice: Subject to any disclaimer, the term of this patent is extended or adjusted under 35 U.S.C. 154(b) by 561 days.

(21) Appl. No.: 10/712,600

(22) Filed: Nov. 13, 2003

(65) Prior Publication Data

US 2004/0138613 A1 Jul. 15, 2004

Related U.S. Application Data

(63) Continuation-in-part of application No. 10/242,976, filed on Sep. 13, 2002, now Pat. No. 6,755,805.

(51) Int. Cl.
*A61M 5/178* (2006.01)
(52) U.S. Cl. .................................. 604/164.08
(58) Field of Classification Search ............... 604/110, 604/192–198, 171, 239, 240, 165.03, 272, 604/264, 164.08; 128/919
See application file for complete search history.

(56) References Cited

U.S. PATENT DOCUMENTS

| | | | |
|---|---|---|---|
| 4,735,618 A | 4/1988 | Hagen | |
| 4,888,001 A | 12/1989 | Schoenberg | |
| 4,944,731 A | 7/1990 | Cole | |
| 5,135,507 A * | 8/1992 | Haber et al. ............... | 604/187 |
| 5,147,319 A | 9/1992 | Ishikawa et al. | |
| 5,192,275 A | 3/1993 | Burns | |
| 5,338,306 A * | 8/1994 | Srivatsa ................ | 604/165.02 |
| 5,445,619 A * | 8/1995 | Burns .................... | 604/192 |
| 5,536,253 A * | 7/1996 | Haber et al. ............. | 604/110 |
| 5,607,398 A | 3/1997 | Parmigiani | |
| 5,713,872 A | 2/1998 | Feuerborn et al. | |
| 5,879,330 A | 3/1999 | Bell | |
| 5,951,522 A | 9/1999 | Rosato et al. | |
| 5,997,504 A | 12/1999 | Bell | |
| 6,156,012 A | 12/2000 | Nathan | |
| 6,210,371 B1 | 4/2001 | Shaw | |
| 6,500,155 B2 | 12/2002 | Sasso | |
| 6,663,604 B1 * | 12/2003 | Huet ...................... | 604/263 |
| 6,830,562 B2 * | 12/2004 | Mogensen et al. ...... | 604/164.12 |
| 7,097,637 B2 * | 8/2006 | Triplett et al. ............. | 604/192 |
| 7,211,069 B2 * | 5/2007 | Lehmann ................ | 604/198 |
| 2002/0111581 A1 * | 8/2002 | Sasso ..................... | 604/93.01 |

OTHER PUBLICATIONS

"Huber Plus Safety Infusion Set", Millennium Medical, MMHP 001/00 REV B, 1 pg.

* cited by examiner

*Primary Examiner*—Kevin C Sirmons
*Assistant Examiner*—Elizabeth R MacNeill
(74) *Attorney, Agent, or Firm*—Daly, Crowley, Mofford & Durkee, LLP (57) ABSTRACT

A medical device, such as a Huber-type device, includes a structure that enhances operator safety by reducing the likelihood that a needle will accidentally injure an operator. In one embodiment, the device includes a collapsible structure that can move from a use position to a non-use position. The device includes first and second wing portions and a channel for covering the needle as it is extracted from the patient. The structure enables the operator to leverage applied pressure for a smooth removal of the needle into the device for safe disposal.

3 Claims, 11 Drawing Sheets

NEEDLE DEVICE HAVING SLIDEABLE MEMBER PROVIDING ENHANCED SAFETY

CROSS REFERENCE TO RELATED APPLICATIONS

This application is a Continuation-in-Part of and claims the benefit of U.S. patent application Ser. No. 10/242,976, filed Sep. 13, 2002, now U.S. Pat. No. 6,755,805 which is hereby incorporated by reference.

STATEMENT REGARDING FEDERALLY SPONSORED RESEARCH

Not Applicable.

FIELD OF THE INVENTION

The present invention relates generally to medical devices and, more particularly, to medical devices having a needle for insertion into a patient.

BACKGROUND OF THE INVENTION

Medical devices for injecting fluids into a patient are well known in the art. One such type of device is generally referred to as implanted ports, which can be implanted subcutaneously in a patient. Various types of ports can be used to provide access to the peritoneal cavity, as well as the vascular, arterial, and epidural systems. The ports typically include a catheter for access to a large vein and a port body having a septum, which is generally formed from silicone.

The port is implanted within a cavity formed in the patient, such as in the chest area, and sutured to underlying tissue. From time to time, it is desirable to refill the port via the septum and/or provide an external source of fluid, e.g., IV access. One type of device used to refill an implanted port is generally known as a Huber needle. Known Huber needles generally include a needle extending from a base structure. With sufficient expertise and experience an operator, such as a nurse, can insert the needle into the port via the septum, which is sliced (not cored) by the needle for self-sealing. The Huber needle can then be taped to the patient and fluid delivered to the patient intravenously as desired via a coupled to the Huber needle device.

However, conventional Huber device can be relatively difficult to remove from the patient. An operator may need to apply a significant amount of force to initiate removal of the device. If the needle suddenly releases, the operator may be accidentally injured by the needle as it is uncontrollably freed from the patient. In addition, even after safe removal, known Huber needle devices can present a hazard due to the outwardly extending needle.

It would, therefore, be desirable to overcome the aforesaid and other disadvantages.

SUMMARY OF THE INVENTION

The present invention provides a medical device, such as a Huber needle, having a needle and a structure that enhances user safety during removal of the needle from a patient. The inventive structure reduces the likelihood that medical personnel will suffer injury from the needle as it is forcibly removed from the patient. While the invention is primarily shown and described in conjunction with a Huber-type needle, it is understood that the invention is applicable to devices in general in which it is desirable to reduce the possibility of injury from a needle.

In one aspect of the invention, a medical device includes a central structural member from which a needle extends. At least one wing portion extends from the central structural member for facilitating removal of the needle from the patient in a controlled manner. A base member for contacting the patient's skin is coupled to the central structural member. First and second members are pivotably secured to the base member so as to provide a structure that can be transitioned from a use position in which the needle extends from the device for insertion into the patient and a non-use position in which the needle is captured by the first member as the needle is extracted from the patient.

With this arrangement, an operator leverages pressure applied to the wing portion(s) with a finger(s) and counter pressure on the first member so as to enable a controlled removal of the needle from the patient. In addition, the collapsible/expandable structure captures the needle in the first member as it is removed from the patient to enhance operator safety.

In another aspect of the invention, a medical device has a use position and a non-use position with a housing having first and second portions each having respective first and second ends. The second portion has a first position in the use position and a second position in the non-use position. A longitudinal member has first and second ends and extends from the housing in the use position. In the non-use position, the longitudinal member is captured by the first housing portion. A needle extends from the device in the use position and envelops the device the non-use position. The device can include one or more locking mechanisms to secure the device in the non-use position.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
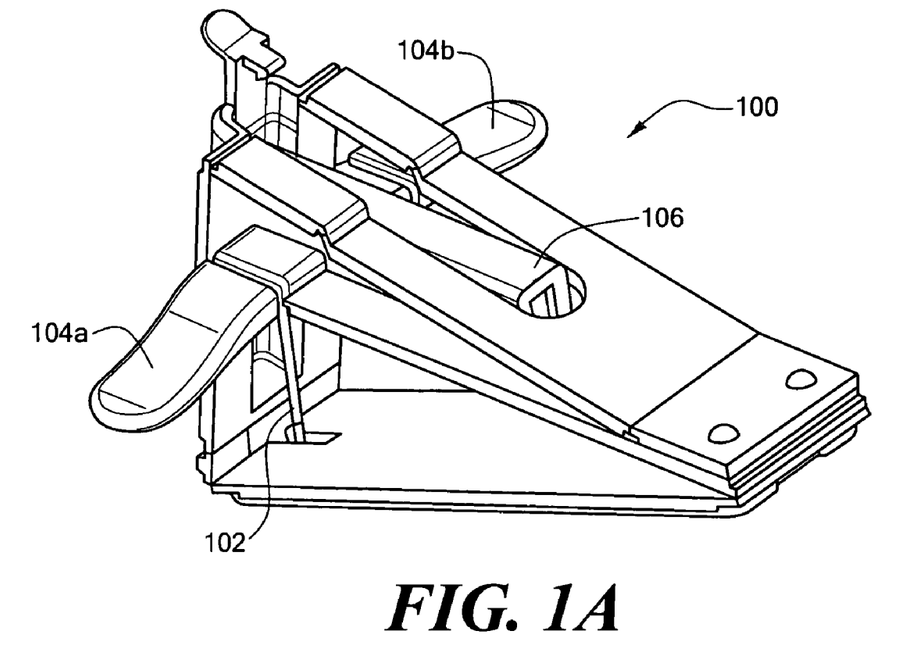
FIGS. 1A and 1B are perspective schematic depictions of a medical device having enhanced safety in accordance with the present invention in the non-use position.
Figure 1B:
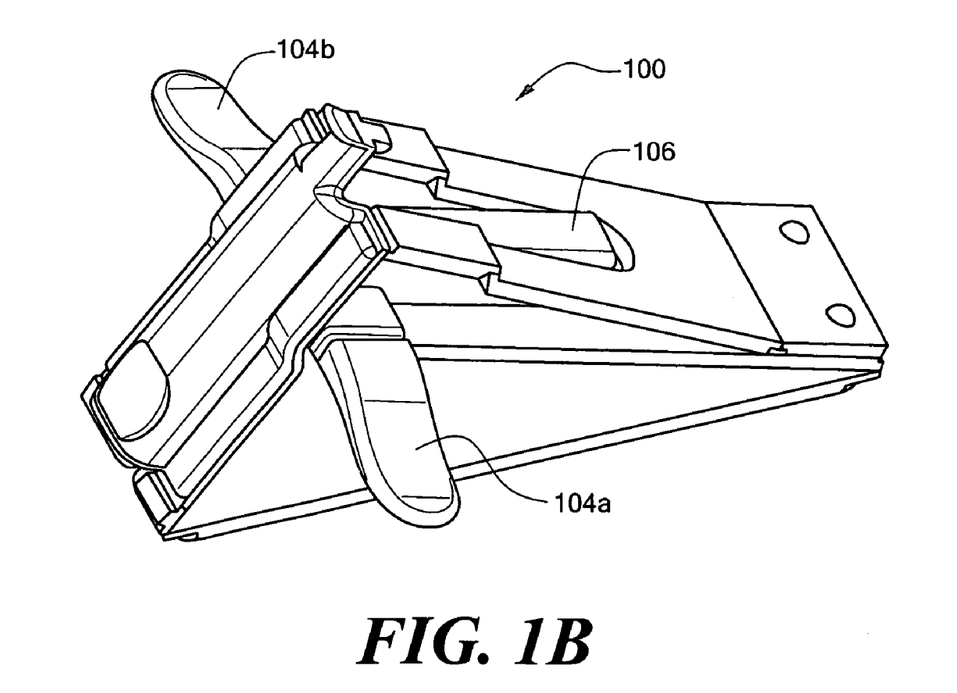

FIGS. 1A-1B show a medical device 100 including a needle 102 and a structure for enhanced operator safety in accordance with the present invention. In general, the device structure facilitates removal of the needle from a patient and captures the needle as it is retracted from the patient's body. During use, the device is relatively flat or collapsed and the needle extends outwardly for insertion into an implanted port device, for example. After use, the device is transitioned to the non-use position in which the needle is captured within the device. As described below, the device can include various features to prevent a transition to the use position from the non-use position to preclude re-use of the device.

The device 100 includes opposed first and second wing portions 104a,b extending from a central structural member 106. As described below, the wing portions 104 provide surfaces on which an operator can apply pressure to insert the device. This arrangement leverages the force applied to the device so as to provide smooth, and safe, insertion and extraction of the needle from the patient.

Figure 2A:
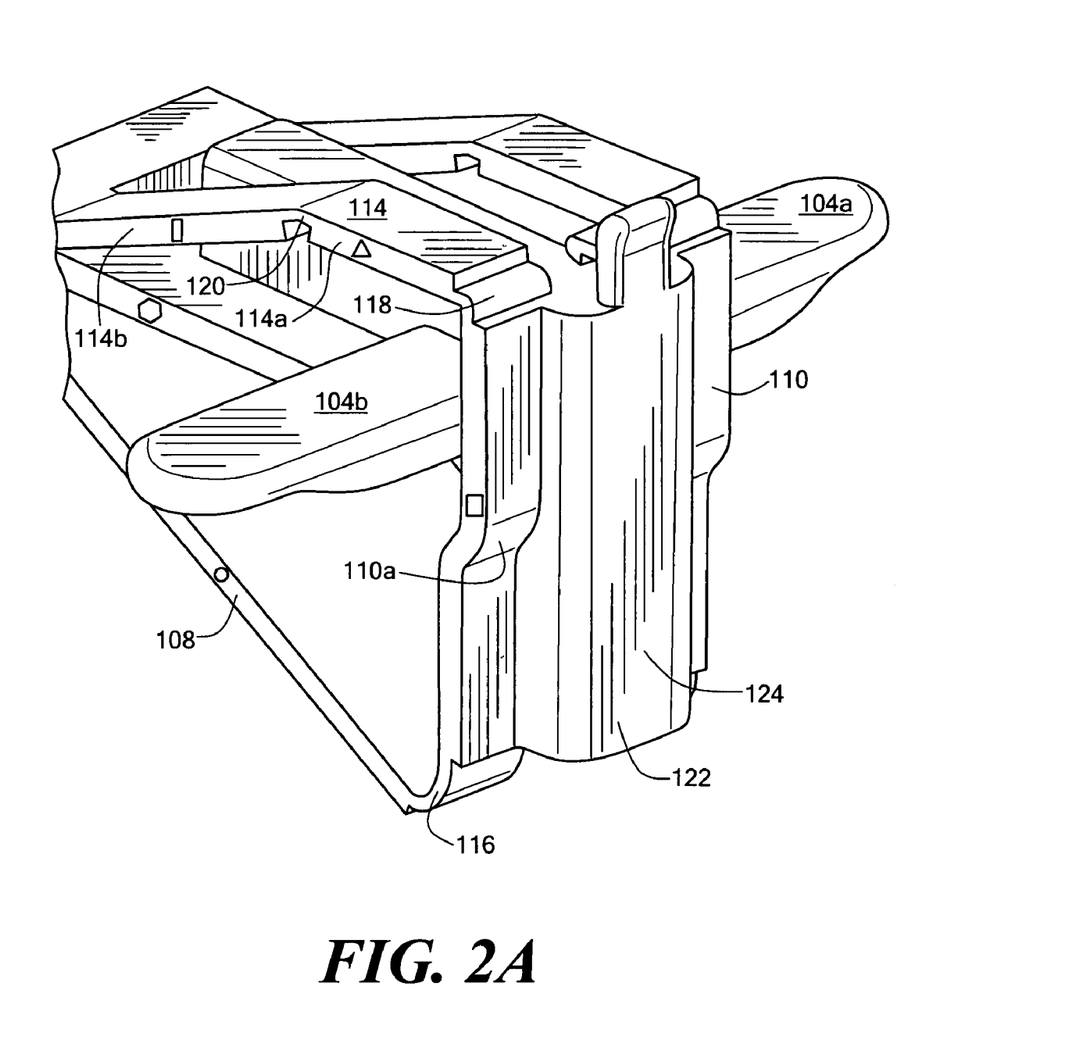
FIG. 2A is a perspective schematic depiction of the medical device of FIG. 1 in the non-use position.
Figure 2B:
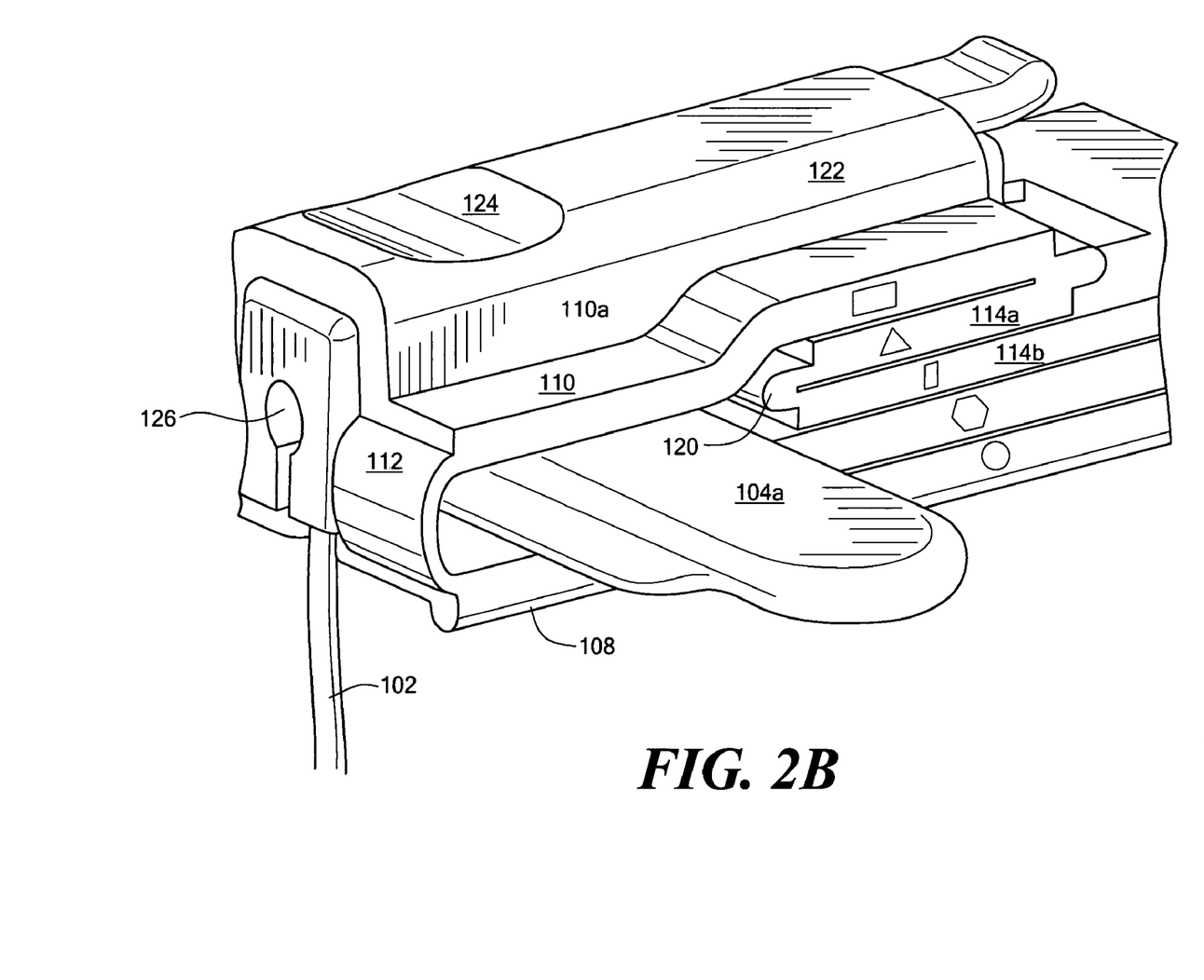
FIG. 2B is a perspective schematic depiction of the medical device of FIG. 2A in a use position.
Figure 2C:
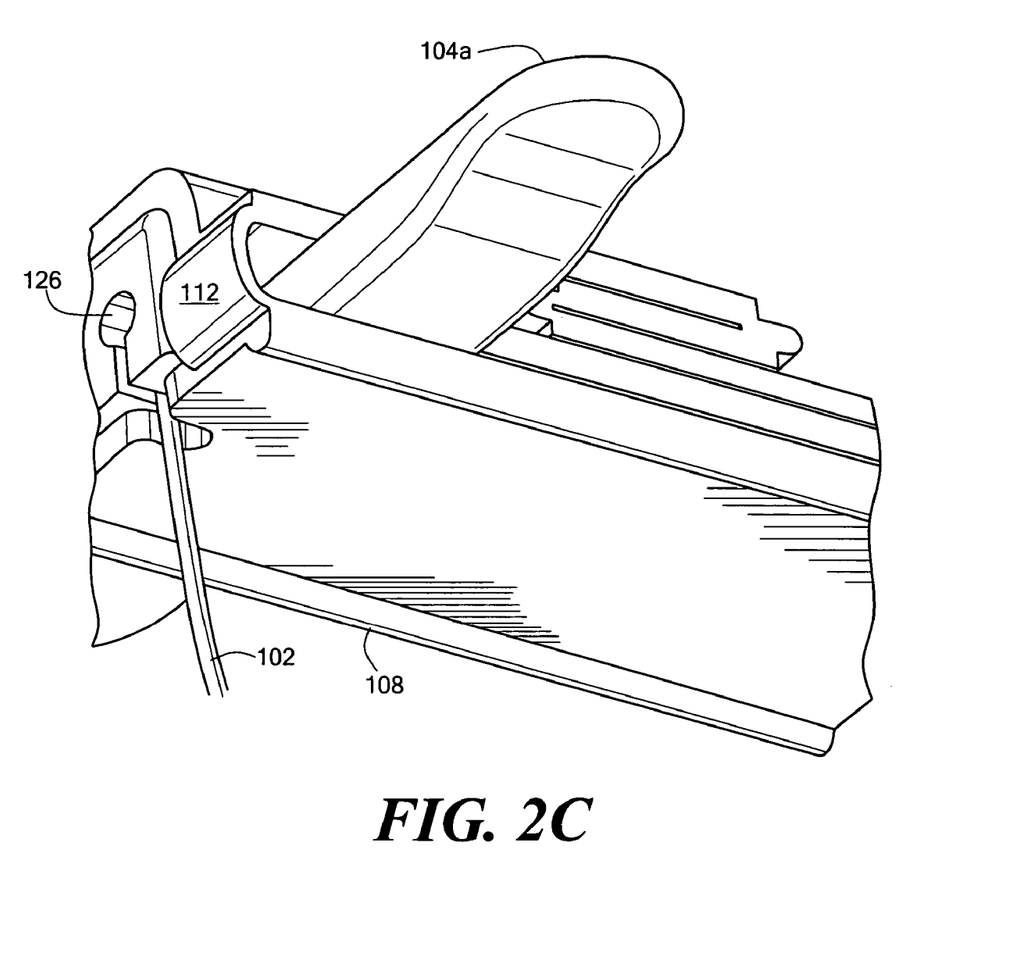
FIG. 2C is a bottom perspective view of the device of FIG. 2B.

FIGS. 2A-2C show further details of an exemplary medical device 100' having a structure providing enhanced safety features in accordance with the present invention. In general, the device of FIGS. 1A and 1B is similar to the device of FIGS. 2A-2C in which like reference designations indicate like elements. The device 100 includes a series of interconnected members that move with respect to the central structural member 106 for safely transitioning the device from use position to the non-use position. The various members shown in FIGS. 2A and 2B are marked with a particular shape as shown to designate the corresponding parts on each of these figures.

A first member 110 is pivotably coupled to a skin-contacting base member 108 at a pivot 112. In an exemplary embodiment, the first member 110 includes an arcuate portion 110a for accommodating the stacked members in the use position, as best shown in FIG. 2B. A second member 114, at respective pivots 116, 118, extends between the base member 108 and the first member 110. In one embodiment, the second member 114 includes first and second sub portions 114a,b joined at a pivot point 120 to enable the second member first and second sub portions 114a,b to fold under the first member 110. It is understood that these members have mirror images on each side of the central structural member 106.

The device further includes a raised portion 122 that can form a part of the first member 110. As shown in FIGS. 2A and 2B, the raised portion 122 can include a depression 124 that can be pressed by a operator's thumb, for example, to insert the device into the patient. As used herein, the use position refers to the needle outwardly extending from the device for insertion into a patient. In the use position, the device is "flat" or collapsed.

As shown in FIGS. 2B and 2C, (and 4C and 5B) for example, the central structural member 106 can include a slotted channel 126 from which the needle extends perpendicularly, for example. The needle 102 can have an L-shape to facilitate coupling of the needle with a tube (not shown) disposed within the channel 126. The needle can be secured within the channel 126 in a conventional manner, such as by adhesive.

The device can include various features to improve the operation and safety of the device. For example, the device can include one or more latches to further enhance operator safety.

Figure 3A:
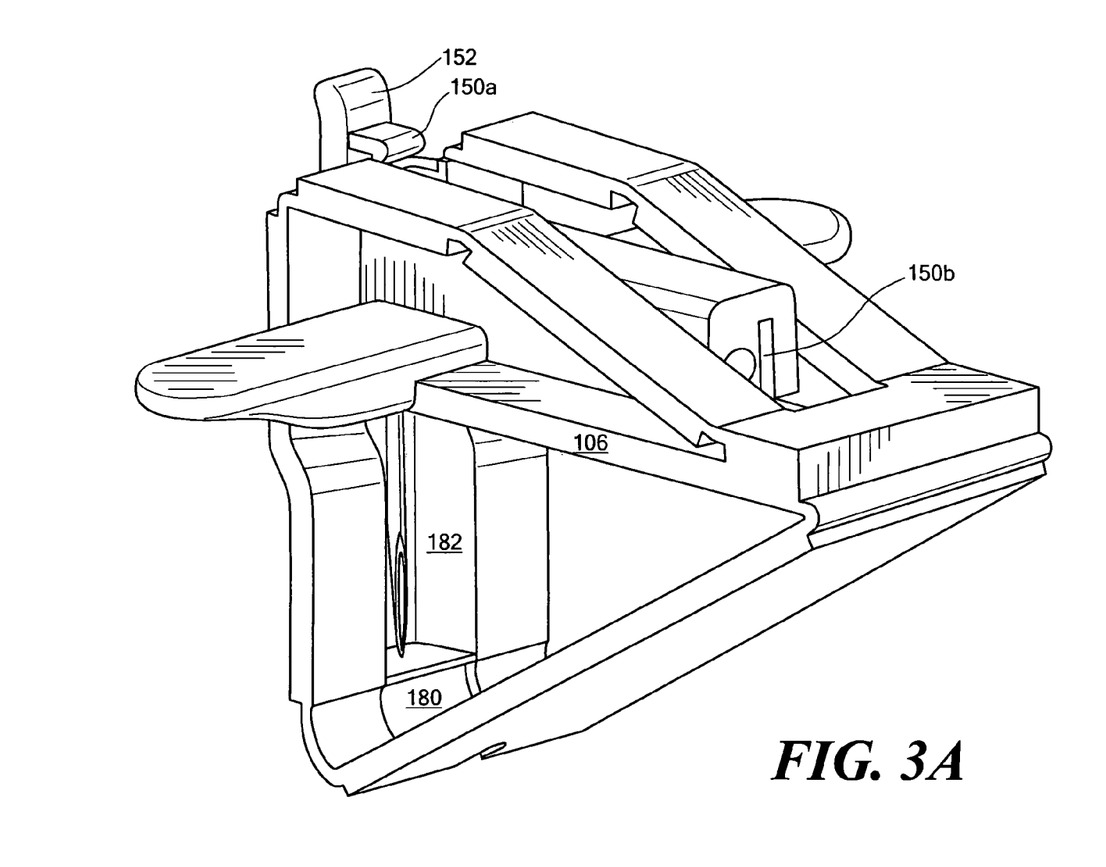
FIG. 3A is a perspective schematic depiction of a medical device having enhanced safety in accordance with the present invention in a non-use position.
Figure 3B:
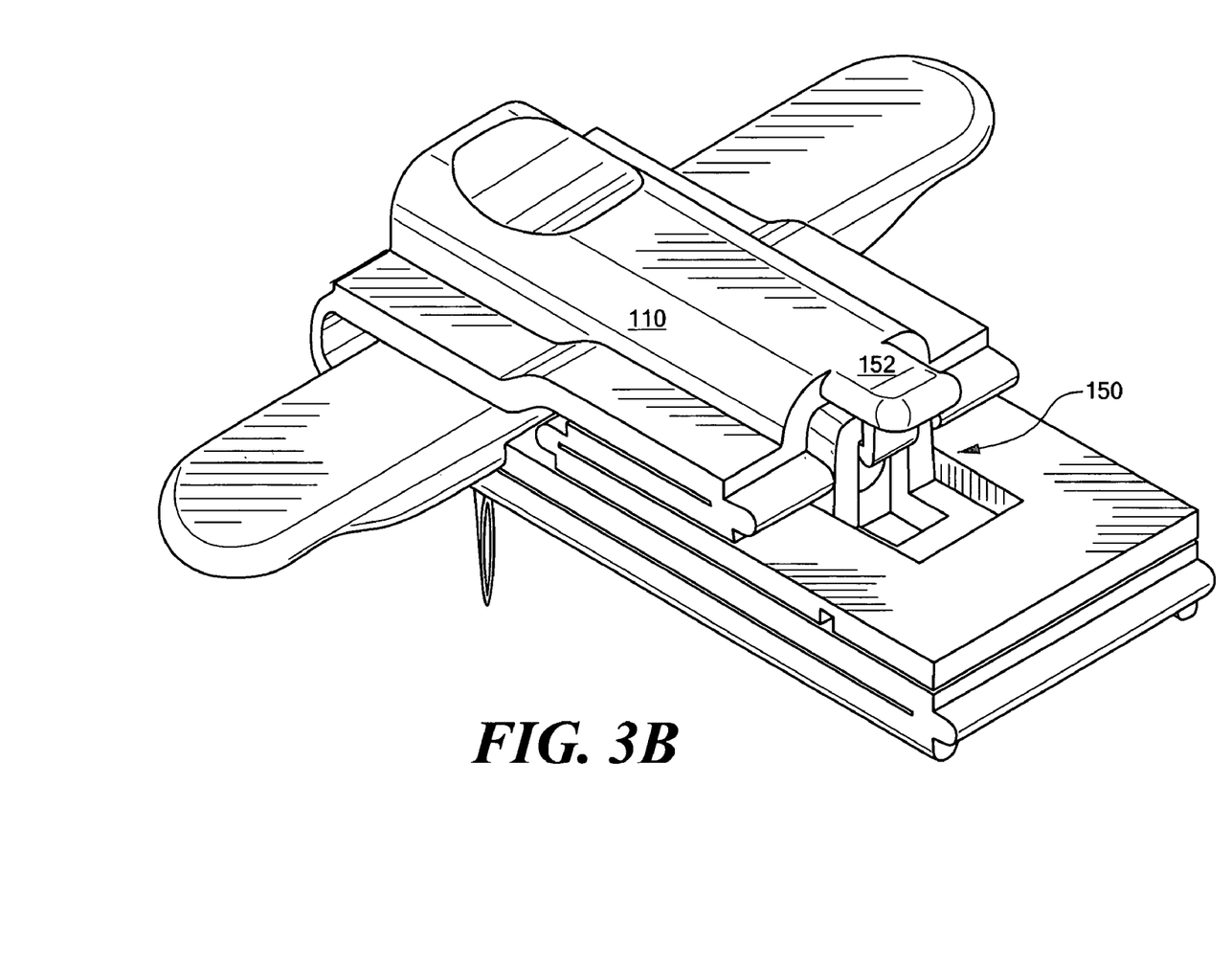
FIG. 3B is a perspective schematic depiction of the medical device of FIG. 3A in the use position.

As shown in FIGS. 3A-3B, the device can include a first latching mechanism 150 located at an end of the first member 110. In one particular embodiment, the first latching mechanism includes a tab 152 to facilitate detachment of a latch member 150a from a receiving aperture or cutout 150b in the central structural member 106. The latching mechanism 150 can be released to raise the first member 110 by lifting the tab 152 prior to removal of the device from the patient.

A second latch 180 shown in FIGS. 3A (and 4C) for example, can be located at a tip of the first member 110 so that the needle is retained within the first member. In an exemplary embodiment, the needle 102 is captured by an arcuate cavity 182 formed in the first member 110. Once the device transitions to the non-use position, the second latch 180 prevents the device from transitioning to the use position by retaining the needle within the cavity.

In another embodiment (not shown), the device can include mechanisms to provide unidirectional movement to the non-use position. In one embodiment, the first member includes a ratchet-type device allowing only movement of the first member 110 away from the base member 108. An exemplary ratchet-type device is shown in FIG. 4C.

Referring again to FIGS. 2A-3B, the structure of the device 100 leverages the force applied to the wing portions 104 and the first member 110 to ease extraction of the needle from the patient. In one embodiment, while the device is flush with the patient's skin, the operator moves the first member 110 to an upright position with respect to the central structural member 106. The operator then applies first and second fingers underneath the wing portions 104 and a thumb, for example, on or near the tab 152 of the first member 110. By applying force on top of the upright first member 110, the implanted port is stabilized in position. The operator can then apply force to lift the wing portions 104 up while applying a counter-force on the first member 110 to leverage the force applied on the wing portions.

The applied pressure forces the central structural member 106 and wings 104 up and away from the base member 108 and the needle 102 retracts into the cavity 182 in first member 110. With this arrangement, it is relatively easy for the operator to apply steady pressure to the device for a smooth extraction of the needle from the patient. That is, the needle is not suddenly freed from the patient in a relatively out of control manner. It is understood that the tab 152 can be shaped to facilitate movement of the first member 110 to an upright position and to accommodate force applied to the tab 152 by the operator's thumb.

Figure 4A:
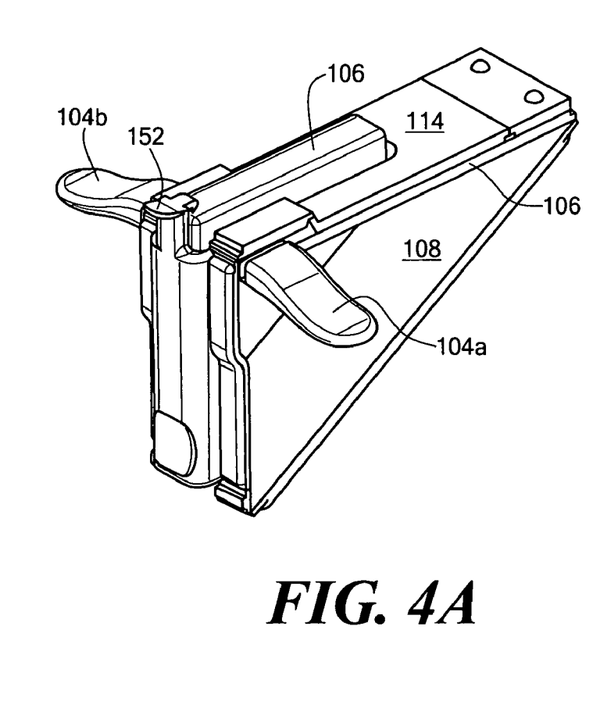
FIG. 4A is a perspective schematic depiction of an exemplary medical device having enhanced safety in accordance with the present invention shown in a non-use position.
Figure 4B:
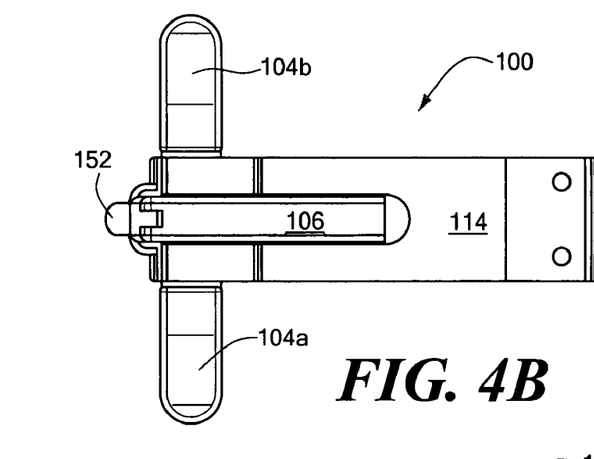
FIG. 4B is a top view of the device of FIG. 4A.
Figure 4C:
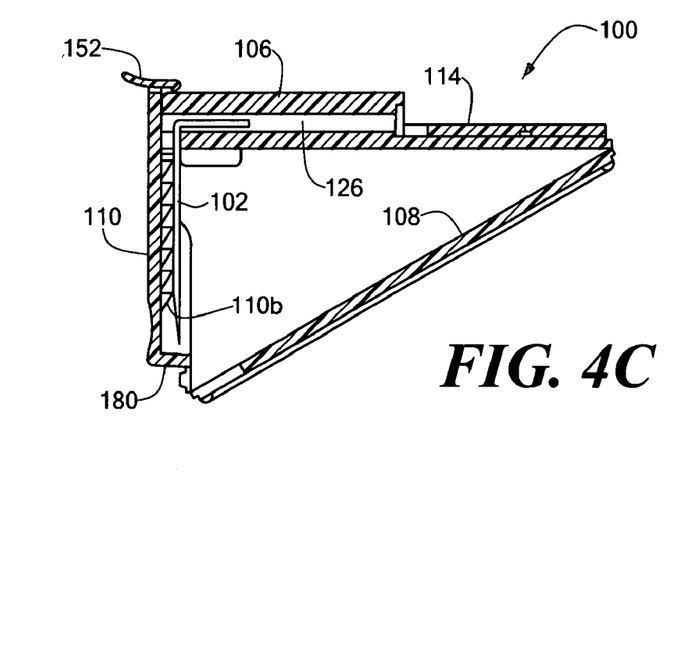
FIG. 4C is a sectional view of the device of FIG. 4B.
Figure 5A:
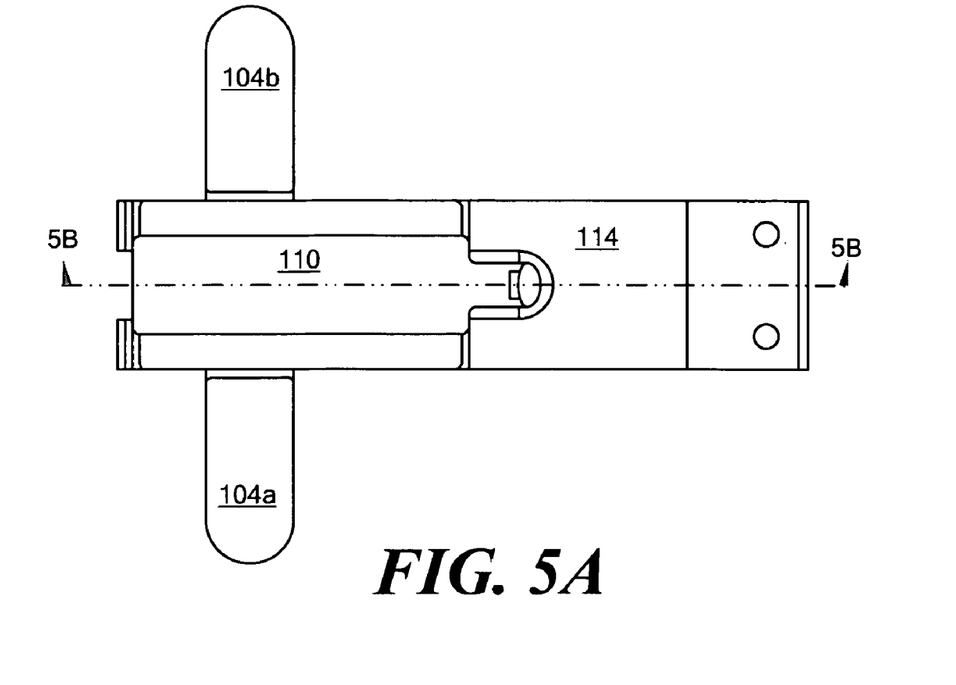
FIG. 5A is a top view of the exemplary medical device of FIG. 4A shown in a use position.
Figure 5B:
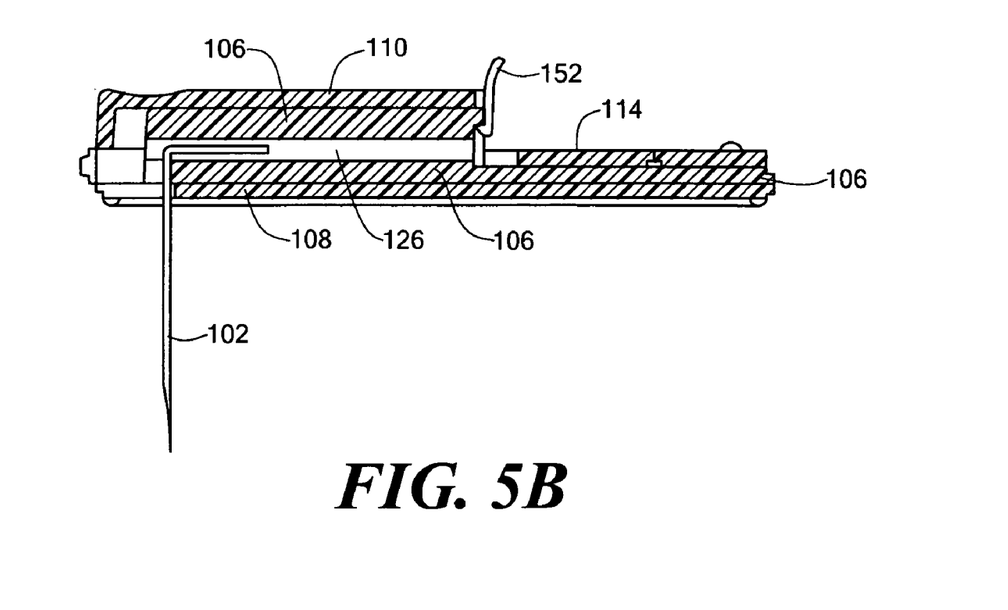
FIG. 5B is a sectional view of the device of FIG. 5A along line 5B.

FIGS. 4A-5B show further details of a Huber needle-type device, such as the device 100 of FIGS. 1A and 1B, having enhanced safety features in accordance with the present invention. FIGS. 4A-4C show a device in the non-use position from a perspective, top, and sectional view, respectively. FIG. 5A is a top view of a device in the use position in accordance with the present invention and FIG. 5B is a sectional view taken along line 5B of FIG. 5A.

In one embodiment, the devices can be delivered in the use position. As described above, the devices can include various features to prevent a transition from the use position to the non-use position. Also, as described above, the devices can include mechanisms to provide unidirectional movement to the non-use position. For example, a ratchet-type feature 110b can be included in the first member 110, allowing the first and second wing portions 104a,b extending from the central structural member 106 to move in only one direction.

Figure 6:
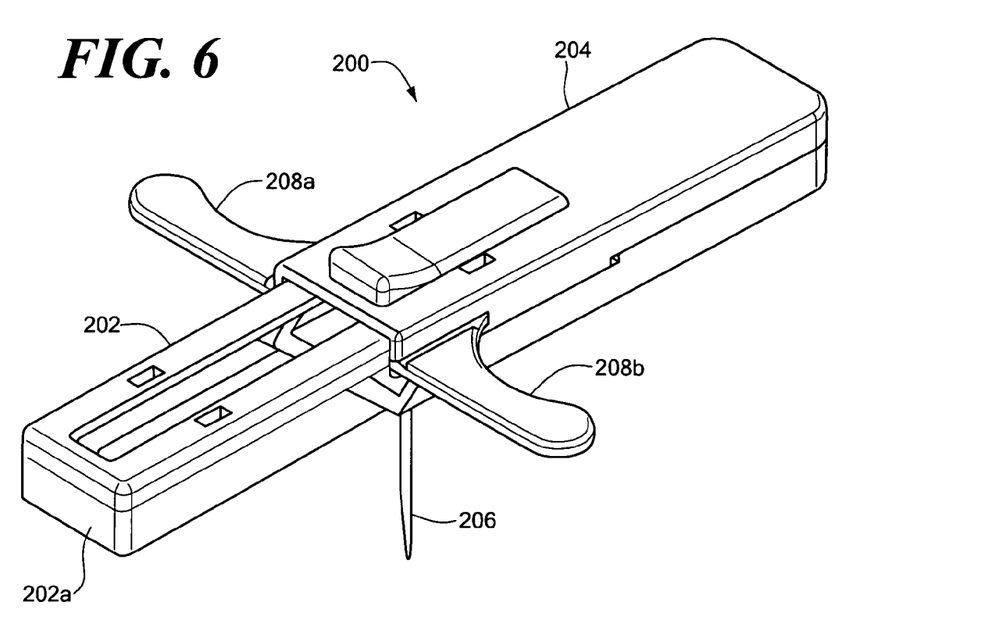
FIG. 6 is a perspective schematic representation of an exemplary medical device shown in a use position in accordance with the present invention.
Figure 7A:
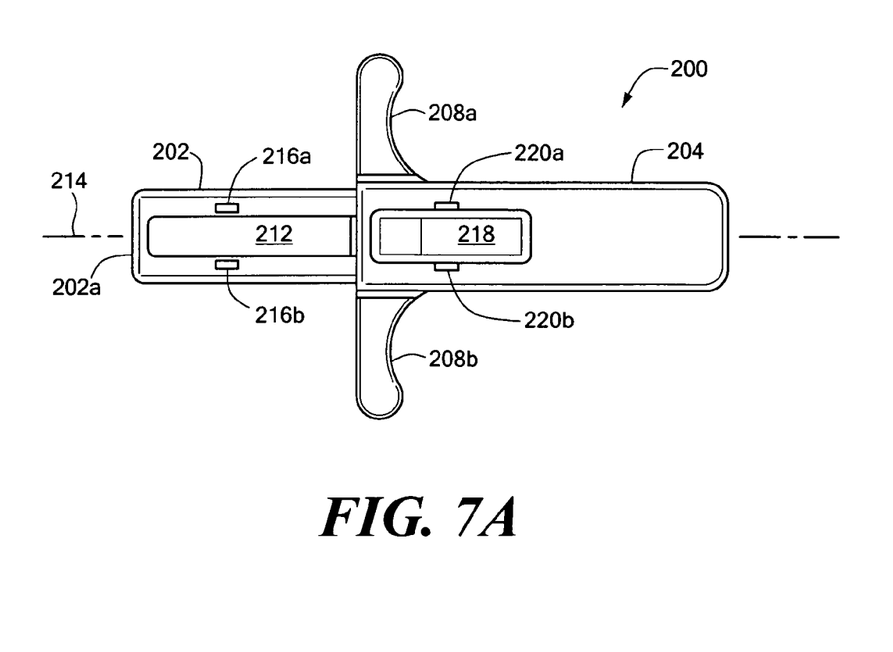
FIG. 7A is a top view of the medical device of FIG. 6.
Figure 7B:
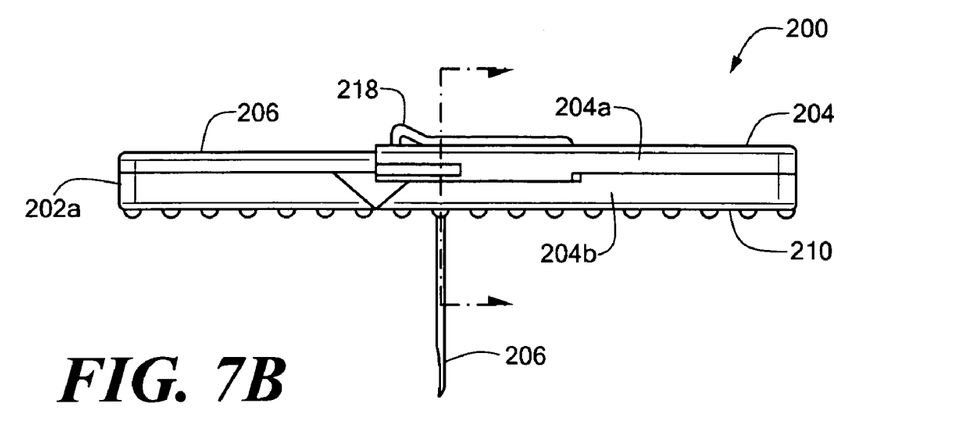
FIG. 7B is a side view of the medical device of FIG. 6.
Figure 7C:
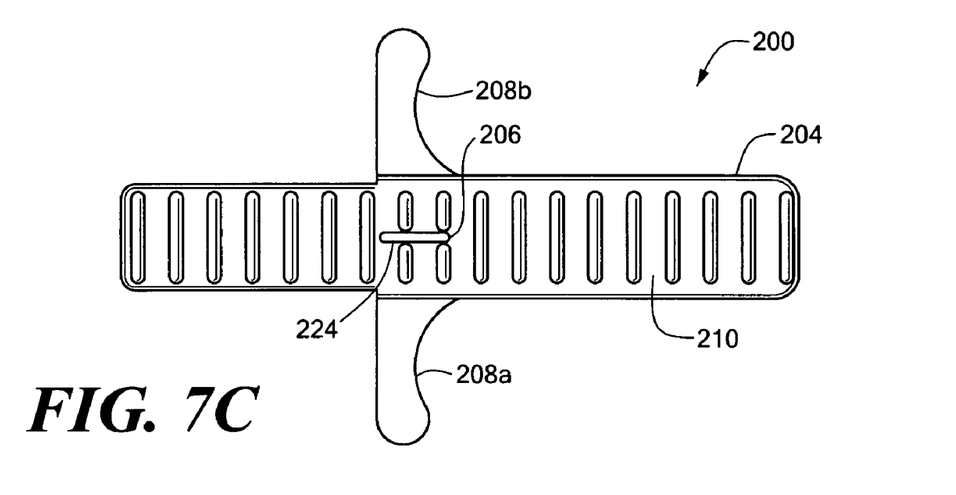
FIG. 7C is a bottom view of the medical device of FIG. 6.
Figure 7D:
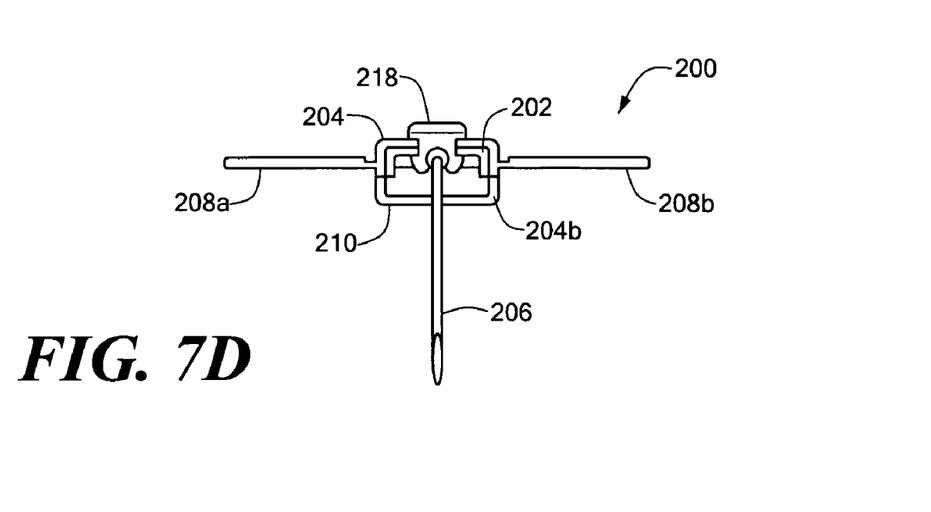
FIG. 7D is a cross-sectional view along line 7D of the medical device of FIG. 7B.

In a further aspect of the invention shown in FIG. 6, a medical device 200, which is shown in a user position, includes a longitudinal member 202 that slides into a housing 204. In an exemplary embodiment, the device 200 locks in a non-use position after removal of a needle 206 from a patient. In general, when the device 200 is in the use position, a user can apply finger pressure to first and second wing portions 208a,b and thumb pressure to an end 202a of the longitudinal member to force retraction of the needle 206 from the patient's body. When the longitudinal member 202 is captured by the housing 204, the needle 206 no longer protrudes from the device 200 to enhance operator safety.

Figure 8A:
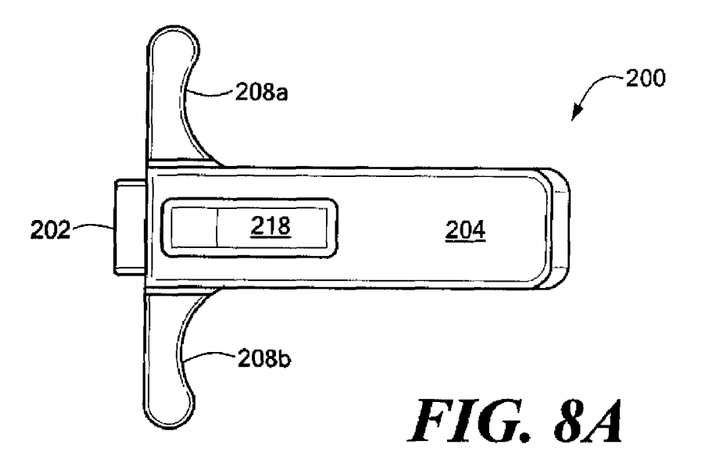
FIG. 8A is a top view of the medical device of FIG. 6 in a non-use position.
Figure 8B:
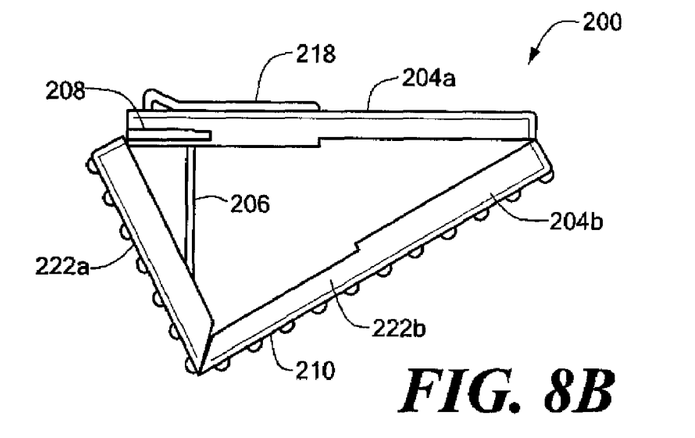
FIG. 8B is a side view of the medical device of FIG. 6 in a non-use position.
Figure 8C:
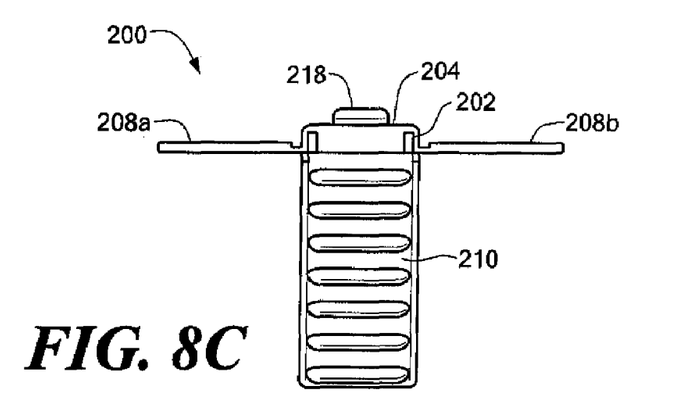
FIG. 8C is a front view of the medical device of FIG. 6 is a non-use position.

FIGS. 7A-8C show further details of the device 200 shown in FIG. 6. FIGS. 7A-7D show the device 200 in a first or use position and FIGS. 8A-8C show the device 200 in a second or non-use position. A user or operator transitions the device 200 from the use position to the non-use position as described in detail below.

As shown in FIGS. 7A-7D, in the use position the needle 206 protrudes from the device 200 for insertion into a patient. The device 200 is relatively flat in the use position so that a bottom surface 210 can rest on a patient while the needle 206 is disposed beneath the skin. The extended longitudinal member 202 includes a channel 212, which can be centered about a longitudinal axis 214 of the device. The needle 206 extends through the channel, which allows axial movement of the longitudinal member. The longitudinal member 202 further includes a first and optional second locking mechanism 216a, 216b for securing the longitudinal member 202 in the non-use position, as described more fully below.

In an exemplary embodiment, the housing 204 include first and second portions 204a, 204b that are secured to each other. In one embodiment, one end of the second housing portion 204b is coupled to one end of the longitudinal member 202 and the other end of the second housing portion is coupled to an end of the first housing portion 204a. Optional first and second wing portions 208a, 208b extend from the housing first portion 204a. The wing portions 208 can be arcuate as shown to receive, for example, the application of force by the index and middle fingers of a user.

A needle retaining member 218 is disposed on the housing 204 for securing the needle 206, which extends through the channel 212, in the longitudinal member 202. The arrangement of the channel 212 and the needle retaining member 218 secures the needle in position while not interfering with movement of the longitudinal member 202 during transition of the device from the use position to the non-use position.

In one embodiment, the housing 204 further includes first and second locking members 220a, 220b that mechanically communicate with the first and second locking members 216a, 216b of the longitudinal member 202. In general, upon complete insertion of the longitudinal member 202 into the housing 204, the housing locking members 220 align and interlock with the longitudinal member locking members 216. In the non-use position, the longitudinal member 202 cannot be removed from the housing 204 to prevent re-use of the device and promote user safety.

FIGS. 8A-8C show the medical device 200 in the non-use position with the longitudinal member 202 fully inserted into housing 204 and the locking members 216, 220 engaged. The second housing portion 204b includes a first piece 222a, and a second piece 222b that can pivot with respect to each other. In the non-use position, the first and second pieces 222 form an angle of about ninety degrees in one particular embodiment. The angled first and second pieces 222 extend outwardly from the first housing portion 204a so as to envelope the needle 206. That is, in the non-use position, the needle 206 does not protrude from the device 200. A slot 224 (FIG. 7C) in the second housing portion 204a enables the first and second pieces 222 to pivot unencumbered by the needle 206.

In one particular embodiment, the non-pivoting end of the first piece 222a is coupled to the end 202a of the longitudinal member. As force is applied to the longitudinal member 202 to force it into the housing 204, movement of the longitudinal member 202 pivots the first piece 222a with respect to the second piece 222b. The non-pivoting end of the second piece 222b is coupled to an end of the first housing portion 204a.

In an exemplary embodiment, the second housing portion 204b includes a series of ribs to create friction as the device 200 transitions to the non-use position during extraction of the needle 206 from the patient. As force is applied to the longitudinal member 202, the pivoting first and second pieces 222 push against the patient to withdraw the needle 206.

It is understood that the device dimensions can vary to meet the needs of a particular application. In one embodiment, the device has a length of about 2.3 inches and a height of about 1.5 inch in the non-use position. The device can have a width measure from ends of the wing portions of about 2.1 inches.

The inventive medical device shown and described herein can be fabricated from a variety of suitable materials well known to one of ordinary skill in the art. Exemplary materials include plastic, such as PVC, polyethylene, and the like.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical device, comprising:
    a housing having first and second housing portions, the first housing portion having first and second ends and the second housing portion having first and second ends, the second housing portion having pivotably coupled first and second pieces, the first housing portion extending along an axis;
    a longitudinal member having first and second ends, a channel, and at least one locking member, the longitudinal member being movable from a use position in which the longitudinal member is extended from the housing along the axis and a non-use position in which the longitudinal member is captured by the first housing portion, the first end of the second housing portion being connected to the first end of the longitudinal member and the second end of the first housing portion being connected to the second end of the second housing portion; and
    a needle extending from a needle retaining member through the channel in the longitudinal member in the use position,
    wherein pressure applied to the longitudinal member in the use position biases the second housing portion away from first housing portion as the first and second pieces of the second housing portion pivot with respect to each other.

2. The device according to claim 1, wherein the longitudinal member includes at least one locking mechanism.

3. The device according to claim 2, wherein the first housing portion includes at least one locking mechanism for engaging the longitudinal member at least one locking member in the non-use position.

* * * * *